US006944491B2

(12) United States Patent
Leveque

(10) Patent No.: US 6,944,491 B2
(45) Date of Patent: Sep. 13, 2005

(54) METHOD OF ACQUIRING AN IMAGE OF A NON-DERMATOGLYPHIC ZONE OF THE SKIN OR OF A ZONE OF THE HAIR BY MEANS OF ACQUISITION APPARATUS INCLUDING A NON-OPTICAL SENSOR

(75) Inventor: Jean-Luc Leveque, Paris (FR)

(73) Assignee: L'Oreal, Paris (FR)

( * ) Notice: Subject to any disclaimer, the term of this patent is extended or adjusted under 35 U.S.C. 154(b) by 565 days.

(21) Appl. No.: 09/909,926

(22) Filed: Jul. 20, 2001

(65) Prior Publication Data

US 2002/0107456 A1 Aug. 8, 2002

(30) Foreign Application Priority Data

Aug. 1, 2000 (FR) .......................................... 00 10144

(51) Int. Cl.[7] .............................................. A61B 5/05
(52) U.S. Cl. ..................................................... 600/407
(58) Field of Search ................................ 600/407, 410, 600/411, 420, 415; 128/2 R; 364/413.1

(56) References Cited

U.S. PATENT DOCUMENTS

| 4,066,068 | A |   | 1/1978  | Nilsson et al. .............. 128/2 R |
| 4,624,264 | A | * | 11/1986 | Sagi ........................... 600/549 |
| 4,849,885 | A |   | 7/1989  | Stillwagon et al. ....... 364/413.1 |
| 5,125,746 | A | * | 6/1992  | Lipshitz ...................... 356/606 |
| 5,935,075 | A |   | 8/1999  | Casscells et al. |
| 6,150,809 | A | * | 11/2000 | Tiernan et al. .............. 324/238 |
| 6,180,867 | B1| * | 1/2001  | Hedengren et al. ......... 136/201 |
| 6,615,071 | B1| * | 9/2003  | Casscells et al. ........... 600/474 |

FOREIGN PATENT DOCUMENTS

| DE | 199 36 097   | 2/2001  |
| EP | 0 748 608    | 12/1996 |
| EP | 1 208 539    | 5/2002  |
| EP | 1 316 912    | 6/2003  |
| FR | 2 821 541    | 9/2002  |
| GB | 2 044 928    | 10/1980 |
| JP | 2001-104050  | 4/2001  |
| WO | WO 01/24700  | 4/2001  |
| WO | WO 02/069802 | 9/2002  |

OTHER PUBLICATIONS

French Search Report dated May 7, 2001 and references which are cited herein.

* cited by examiner

Primary Examiner—Daniel Robinson
(74) Attorney, Agent, or Firm—Oblon, Spivak, McClelland, Maier & Neustadt, P.C.

(57) ABSTRACT

The invention relates to a method of acquiring an image of a non-dermatoglyphic zone of the skin or the hair by means of acquisition apparatus comprising a non-optical sensor.

54 Claims, 1 Drawing Sheet

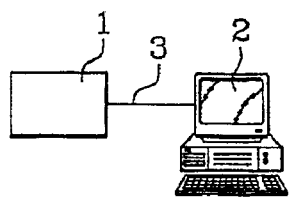
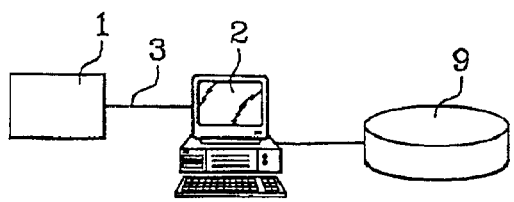
Fig. 1          Fig. 2
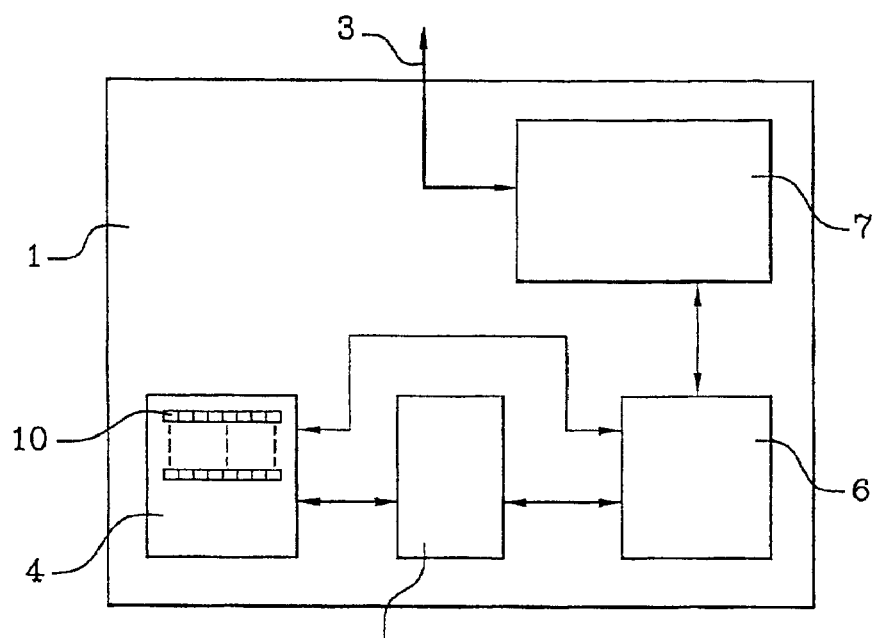
Fig. 3
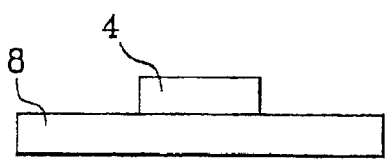
Fig. 4
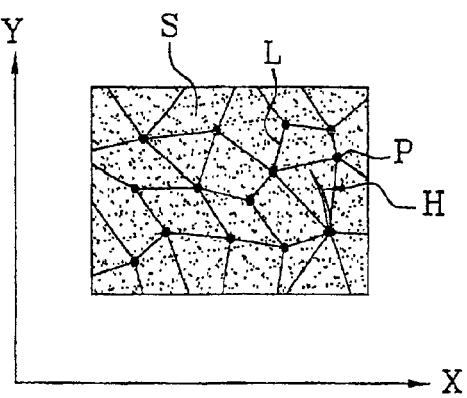
Fig. 5

METHOD OF ACQUIRING AN IMAGE OF A NON-DERMATOGLYPHIC ZONE OF THE SKIN OR OF A ZONE OF THE HAIR BY MEANS OF ACQUISITION APPARATUS INCLUDING A NON-OPTICAL SENSOR

The present invention relates to observing human skin or hair, in particular for the purpose of diagnosis and, where appropriate, of recommending suitable treatment.

The invention relates more particularly, but not exclusively, to a method enabling certain parameters of a non-dermatoglyphic zone of the skin or of a zone of the hair to be determined, and/or to establish a diagnosis.

BACKGROUND OF THE INVENTION

The term "non-dermatoglyphic zone of the skin" should be understood, in the meaning of the present invention, as being a zone of the skin which is substantially free from dermatoglyphs, which do not deteriorate with age. Dermatoglyphs are present in the palm regions, in particular at the ends of the fingers where they constitute fingerprints. Zones of the skin that do not have dermatoglyphs deteriorate with age and present folding of mechanical origin, in the form of ridges or furrows, some of which are known as wrinkles.

There exists a need for means that are relatively simple and inexpensive for informing a person about the state of the skin or the hair in order to determine whether cosmetic care is necessary.

Such means must be relatively simple and inexpensive in order to be used on a large scale.

There also exists a need for facilitating selection of care that is appropriate given the nature and/or the state of the skin or the hair of a given person.

There also exists a need to have means available capable of revealing the initial effects of treatment on the skin or the hair, essentially in order to encourage the person being treated to continue with the treatment.

British patent application GB-A-2 288 511 describes a system seeking to establish remote diagnosis and including an optical camera.

The image of a skin anomaly is acquired by the camera and is then sent in digital format to a remote consultation center where a dermatologist can consult it and give a diagnosis.

Such a system requires intervention by a doctor.

Furthermore, its cost is relatively high because a camera is used, and no cosmetic application for the system is mentioned.

OBJECTS AND SUMMARY OF THE INVENTION

The invention seeks in particular to satisfy all or some of the above-mentioned needs.

The invention achieves this by means of a novel method of acquiring an image of a non-dermatoglyphic zone of the skin or of a zone of the hair in order to determine certain parameters of said region and/or make a diagnosis, wherein the image is acquired by means of acquisition apparatus comprising at least one non-optical sensor.

Such a non-optical sensor can obtain information concerning the microrelief of said zone.

The term "non-optical sensor" is used in the meaning of the present invention to designate a sensor capable of providing useful information in response to excitation that does not involve visible light, and preferably without using focusing means such as lenses.

The non-optical sensor can in particular be a non-thermal sensor.

The term "image" is used to mean a set of data and/or signals representative of the appearance of the zone under study.

The term "microrelief" is used to mean microscopic relief at the surface of the skin or the hair, associated in particular with the presence of folding such as wrinkles large and small, pores, dead cells, hairs, scales, and relief associated, for example, with the skin being dry.

The Applicant has found, unexpectedly, that it is possible to use an image acquired by a non-optical sensor to derive information that is useful for determining certain parameters of the skin or of the hair and/or for establishing a diagnosis of the state of the skin or of the hair and/or for revealing the result of cosmetic or other treatment.

One advantage of the invention, amongst others, lies in the fact that the cost of a non-optical sensor can be considerably less than that of an optical sensor and can consequently be compatible with mass marketing, and not restricted to the professional market.

In a particular implementation of the invention, the acquisition apparatus includes a non-optical sensor having an active surface that is sensitive to temperature variations.

In another particular implementation of the invention, the acquisition apparatus includes a sensor having an active surface that is sensitive to at least one electrical magnitude, e.g. electrical charge.

This electrical magnitude can be measured, for example, by measuring capacitance or conductance.

In another particular application of the invention, the acquisition apparatus includes an active surface that is sensitive to variations in pressure.

The active surface is preferably defined by a plurality of individual detection cells occupying at least one row, and preferably occupying a plurality of juxtaposed rows.

In general, the greater the density of individual detection cells per unit area, the better the resolution.

Preferably, the acquisition device is arranged to deliver the image of the observed zone in digital form, which makes it easier, for example, to transmit the image to a microcomputer and/or over a network, in particular over the Internet.

Also preferably, the acquisition apparatus is arranged to acquire an image of a zone that is large enough to be representative in a statistical sense, e.g. having an area that preferably lies in the range about 0.2 square centimeters ($cm^2$) to about 2 $cm^2$, and more preferably lying in the range 0.25 $cm^2$ to about 1 $cm^2$.

By way of example, image acquisition can be performed statically, without relative displacement between the sensor and the zone under study.

In general, static acquisition is possible whenever the active surface has a large number of individual detection cells disposed in a plurality of juxtaposed rows.

In a variant, acquisition can be performed dynamically, with the sensor and the zone under study moving relative to each other.

Such dynamic acquisition is preferable when the active surface is in the form of a strip of individual detection cells, with the relative displacement between the zone under study and the sensor then preferably taking place perpendicularly to the long direction of the strip.

The acquired image can be a two-dimensional (2D) image of the zone under study, it being understood that a 2D image can nevertheless provide a large amount of useful information.

Nevertheless, by making a plurality of simultaneous acquisitions both of sensor contact pressure and of the image of the zone under study, it is sometimes possible to extract additional information about the structure of the microrelief of the zone under study.

The image which is acquired can thus be a three-dimensional (3D) image of the zone under study when the sensor and/or its environment make that possible.

Image acquisition can be performed without the sensor coming into contact with the zone under study (e.g. by means of an electric field effect), or in a variant with the sensor coming into contact with the zone under study.

When image acquisition is performed with contact between the zone under study and the sensor, it is advantageous to measure the contact pressure between the sensor and the zone under study during image acquisition, since the contact area between the zone under study and the sensor, and therefore the resulting image, can vary as a function of contact pressure.

When contact pressure between the zone under study and the sensor is not measured, it is preferable for image acquisition to be performed with contact pressure that is substantially constant.

The spatial resolution of the sensor preferably lies in the range 10 micrometers ($\mu$m) to 100 $\mu$m, more preferably in the range 25 $\mu$m to 75 $\mu$m, and more preferably still is about 50 $\mu$m. In particular, the sensor can present resolution enabling it to detect portions in relief that are as small as 100 $\mu$m, or even smaller.

This resolution corresponds substantially to that of the sensors that are the most widespread which have an active surface responsive to electrical charge or to temperature variations and that are used for recognizing fingerprints, and that are consequently likely to be manufactured in large quantities at relatively low cost.

In a preferred implementation of the invention, the acquired image is processed in order to determine parameters that are characteristic of the zone under study.

The processing that is performed is preferably digital processing that does not require the intervention of a human operator, in particular of a doctor.

Such processing can then be performed entirely automatically, quickly, and at low cost.

The image processing that is performed seeks, for example, to determine one or more magnitudes that are characteristic of the microrelief of the skin so as to be able to deduce information therefrom about the state of the skin (where the measured magnitude(s) can optionally be combined, where appropriate, with data supplied by the person concerned concerning age, sex, or ethnic type), with the resulting information relating, for example, to the probable concentration in the skin of macromolecules forming the extra-cellular matrix of conjunctive tissue, i.e. collagen, elastin, proteoglycans, and glycoproteins, and/or concerning the orientations of collagen bundles relative to the axis of an arm, amongst other things.

The image processing which is performed also seeks to provide information concerning the density of skin lines and more particularly the anisotropy coefficient of line density, i.e. the ratio of line density in a first direction to line density in a second direction, substantially perpendicular to the first.

The processing performed on the image can also seek to determine the number and the size of pores in the skin, or indeed the size and/or the density of the plateaus as defined by the lines.

The processing performed on the image can also serve to quantify and/or characterize the wrinkles present in the skin and to give information concerning pilosity.

The result of the processing performed on the image preferably makes it possible to establish a diagnosis or include a diagnosis which, as mentioned above, can take account of factors such as the surface density of skin lines, the anisotropy coefficient of line density, the surface density and/or the size of pores, and/or the density and/or the size of plateaus.

The result of the processing also preferably makes it possible to recommended cosmetic care product, i.e. a substance for cosmetic use that can be obtained without medical prescription.

Image processing can be performed remotely by transferring digital data over a network, in particular the Internet.

Image processing can also be performed on site, using a microcomputer or any other suitable computation means connected to the acquisition apparatus.

Images of the skin or of the hair and/or data associated with said images can be taken at successive points in time and stored on a recording medium.

Images taken at different times and/or data associated with said images can then be displayed simultaneously or consecutively at short time intervals in order to enable the person whose skin is under study to see the initial effects of treatment or to observe deterioration and the need for treatment.

A database can be consulted during image processing in order to compare the acquired image and/or associated data with stock images or data taken from a large population in order to make it easier to establish a diagnosis.

The zone of the skin that is studied can be a region of the forearm or a region of the face (including the lips), e.g. the cheeks.

Image processing can also serve to determine a mean hair diameter when the zone under study is situated on the scalp.

The invention also provides an assembly comprising:

image acquisition apparatus for acquiring an image of a non-dermatoglyphic zone of the skin or a zone of the hair in order to determine certain parameters of said zone and/or perform a diagnosis, said acquisition apparatus including a portable non-optical sensor arranged to be suitable for being brought into contact with a non-dermatoglyphic zone of the skin, in particular a region of the forearm or of the face, or with a zone of the hair, preferably having an active surface that is sensitive to temperature variations, to electrical charge, or to variations in pressure; and a computer tool enabling useful information to be extracted from the signals delivered by the sensor concerning the microrelief of said zone, said information relating to the state of the skin or of the hair.

The invention also provides a computer system, in particular an Internet server, arranged to:

a) receive images in digital form corresponding to a non-dermatoglyphic zone of the skin or to a zone of the hair;

b) process said images in order to determine data concerning the surface density of lines and/or the surface density of pores and/or the size of pores and/or the anisotropy coefficient of the line density;

c) establish a diagnosis on the basis of the data resulting from the image processing, optionally making use of comparison data; and d) optionally, on the basis of said diagnosis, selecting a suitable care product from a predetermined range of products.

Advantageously, the computer system is also arranged in such a manner as to send an e-mail or other message to a person who has made a connection and transmitted an image of the skin, said e-mail or message informing the person about the result of the diagnosis and optionally recommending a care product.

The invention also provides a method of remote diagnosis for non-therapeutic purposes, consisting in supplying a user with detection apparatus suitable for connection to a microcomputer and/or a network, in particular the Internet, in enabling the user to acquire an image of a non-dermatoglyphic zone of the skin by means of said acquisition apparatus, in enabling the user to send said image in digital form to a remote processing center via said network, in performing diagnosis in said processing center, in informing the user by e-mail or by any other method of transmission about the result of the diagnosis, and optionally in recommending cosmetic care and, where appropriate, in delivering to the user one or more suitable care products.

The person preferably uses the network to send an image of the skin to the processing center together with personal data for facilitating the establishment of a diagnosis, such as age, sex, nature of care products previously used, or ethnic type, where this list is not exhaustive.

The invention also provides a method of cosmetic treatment comprising the following steps:

a) acquiring an image of a non-dermatoglyphic zone of the skin or of a zone of the hair, by means of a non-optical sensor;

b) processing said image in a computer system so as to obtain a diagnosis; and c) recommending care treatment in the light of said diagnosis.

The method can also include a step consisting in applying the recommended care product on the zone in question.

In a particular implementation of this cosmetic treatment method, the image is processed at its site of acquisition, e.g. in premises for selling or presenting goods, or at home.

In another particular implementation of this method of cosmetic treatment, the image is processed remotely, in a processing center.

Under such circumstances, the image is advantageously sent to the processing center via a network, in particular the Internet.

This cosmetic treatment method preferably also comprises the step in consisting in storing images acquired successively in time or the data that results therefrom so as to make comparisons and show up any improvements, for example.

BRIEF DESCRIPTION OF THE DRAWINGS

Other characteristics and advantages of the present invention will appear on reading the following detailed description of non-limiting implementations of the invention, and on examining the accompanying drawing, in which:

FIG. 1 is a diagram of a microcomputer connected to acquisition apparatus constituting a non-limiting embodiment of the invention;

FIG. 2 is a view analogous to FIG. 1 showing the microcomputer connected to a remote processing center;

FIG. 3 is a block diagram showing one possible arrangement of the acquisition apparatus;

FIG. 4 shows the sensor mounted on a pressure-sensitive support; and

FIG. 5 shows an image of the skin obtained by means of a non-optical sensor.

MORE DETAILED DESCRIPTION

FIG. 1 shows acquisition apparatus 1 of the invention connected to a microcomputer 2 via a data transmission cable 3.

The acquisition apparatus 1 is preferably implemented in miniature form, so as to make it easier to incorporate in a housing of small dimensions that can easily be handled and brought into contact with or into the immediate vicinity of the zone to be studied, e.g. a zone situated on the face or on the forearm.

As shown in FIG. 3, the acquisition apparatus 1 can comprise a non-optical sensor 4 connected to an analog-to-digital converter 5 and to a control circuit 6 controlling operation of the sensor 4.

The control circuit 6 is itself connected to an interface circuit 7 enabling digital data to be exchanged with the microcomputer 2.

The sensor 4 has an active surface that is responsive to temperature, for example, and that is defined by a plurality of juxtaposed individual detection cells 10.

Active surfaces of this type are commercially available, in particular from Atmel, under the trade name FINGER CHIP (registered trademark).

The sensor 4 can also comprise an active surface defined by a plurality of juxtaposed capacitive individual detection cells.

Active surfaces of this type are sold, for example by SGS-Thomson Microelectronics under the trade name TOUCH CHIP (registered trademark).

Other examples of non-optical sensors are to be found in U.S. Pat. Nos. 4,353,056 and 5,864,296, in particular.

FIG. 5 shows a 2D image of map obtained using a strip of individual detection cells defining a temperature sensitive active surface and moved in contact with the forearm of a person.

On examining this figure, the person skilled in the art will understand that the resulting image gives information about the state of the skin.

In particular, there can be seen pores P, and lines L surrounding plateaus S, and also hairs H.

The person skilled in the art will readily understand that such an image can be subjected to processing making it possible to determine the surface density of the lines L and the anisotropy coefficient of this density, i.e. the ratio of the density of lines L in an X direction to the density of lines L in a Y direction perpendicular thereto.

This ratio varies with age and gives information concerning the aging state of the skin, for example.

Image processing can easily be performed by suitable software loaded into the microcomputer 2, said software also advantageously being arranged to give a diagnosis and recommend a care product.

As shown in FIG. 2, the microcomputer 2 can also be connected by means of a modem to a remote processing center 9 comprising a server incorporating a database or suitable for communicating with a database.

The processing center 9 can be made accessible to the user by means of an Internet site, for example.

In the example of FIG. 2, the user sends the image of the skin as obtained by means of the acquisition apparatus 1 to the processing center 9, and the center processes the data it receives so as to deliver a diagnosis and possibly recommend a care product.

The microcomputer 2 and/or the processing center 9 are preferably arranged to store images that are acquired in succession, so as to enable a user to observe quickly the effects of a care product, for example.

A user can thus be encouraged to continue with treatment once signs of improvement appear, even if they are invisible to the naked eye and not perceptible to an untrained person, or on the contrary the user can change treatment when it turns out to be ineffective.

The microcomputer 2 is advantageously programmed to be capable of displaying a plurality of images of the skin, taken at different times, so as to enable users to make their own comparisons.

The microcomputer 2 could also be arranged to contribute to showing up changes in the microrelief of the skin between two images taken at different times.

In the examples described above, it is necessary to make contact between the zone under study and the sensor while acquiring the image.

Nevertheless, the invention is not limited to sensors that require contact with the zone to be observed.

When contact is necessary and the image delivered by the sensor changes with changing pressure exerted by the sensor on the observed zone, it is advantageous, as shown in FIG. 4, to use a suitable detector 8 on which the sensor 4 is mounted to measure the contact pressure associated with each image so as to extract 3D information from the way images vary with pressure.

This makes it possible with suitable data processing to determine the profile of a wrinkle, for example.

Naturally, the invention is not limited to the examples described above.

In particular, the acquisition apparatus can be used to measure mean hair diameter, for example.

What is claimed is:

1. A method of acquiring an image comprising:
   providing at least one non-optical sensor for obtaining information concerning microrelief of a zone; and
   utilizing said at least one non-optical sensor to acquire an image of one of a non- dermatoglyphic zone of skin and a zone of hair.

2. A method according to claim 1, wherein the non-optical sensor includes a sensor having an active surface that is sensitive to variations in temperature.

3. A method according to claim 1, wherein the non-optical sensor includes a sensor having an active surface sensitive to an electrical property measured by measuring one of capacitance and conductance.

4. A method according to claim 1, wherein the non-optical sensor includes a sensor having an active surface that is sensitive to variations in pressure.

5. A method according to claim 2, wherein the active surface is defined by a plurality of individual detection cells disposed in at least one row.

6. A method according to claim 5, wherein the acquisition apparatus is arranged to deliver the image in digital form.

7. A method according to claim 1, wherein the acquisition apparatus is arranged to acquire an image of a zone that is large enough to be statistically representative, including an area lying in a range of from about 0.2 cm2 to about 2 cm2.

8. A method according to claim 1, wherein the image is acquired statically, without moving the non-optical sensor relative to the zone under study during image acquisition.

9. A method according to claim 1, wherein the image is acquired dynamically, with relative movement between the non-optical sensor and the zone under study during image acquisition.

10. A method according to claim 9, wherein the non-optical sensor includes an active surface in the form of a strip of individual detection cells.

11. A method according to claim 1, wherein the image is acquired without the non-optical sensor coming into contact with the zone under study.

12. A method according to claim 1, wherein the image is acquired with the non-optical sensor in contact with the zone under study.

13. A method according to claim 12, including measuring pressure of contact between the non-optical sensor and the zone under study during image acquisition.

14. A method according to claim 12, wherein the image is acquired at a substantially constant contact pressure.

15. A method according to claim 1, wherein the acquired image is a three dimensional image of the zone under study.

16. A method according to claim 1, wherein the acquired image is a two dimensional image of the zone under study.

17. A method according to claim 1, wherein the non-optical sensor has a spatial resolution lying in a range of from 10 $\mu$m to 100 $\mu$m.

18. A method according to claim 1, further including processing the image in order to determine characteristic parameters of the zone under study.

19. A method according to claim 18, wherein the processing provides information concerning a surface density of skin lines.

20. A method according to claim 18, wherein the processing provides information concerning an anisotrophy coefficient of skin line density.

21. A method according to claim 18, wherein the processing provides information concerning the number and the size of skin pores.

22. A method according to claim 18, further including utilizing a result of the processing to establish a diagnosis.

23. A method according to claim 18, further including utilizing a result of the processing to recommend a care treatment.

24. A method according to claim 18, wherein the processing is performed remotely by transmitting digital data over a network.

25. A method according to claim 1, further including storing at least one of a plurality of the images and data associated with a plurality of the images on a recording medium, and wherein the plurality of images are taken at different times.

26. A method according to claim 1, further including simultaneously displaying at least one of a plurality of the images and data associated with a plurality of the images, and wherein the plurality of images are taken at different times to enable a person to evaluate effects of treatment or the need for treatment.

27. A method according to claim 1, wherein the zone under study includes one of a region of the forearm and a region of the face.

28. A method for recommending cosmetic treatment, the method comprising:

a) acquiring an image of at least one of a non-dermatoglyphic zone of the skin and a zone of the hair utilizing a non-optical sensor;

b) processing said image in a computer system so as to obtain a diagnosis; and c) recommending care treatment in response to said diagnosis.

29. A method according to claim 28, wherein the image is processed at a site at which said image is acquired.

30. A method according to claim 28, wherein the image is process at a processing location remote from a site at which said image is acquired.

31. A method according to claim 30, wherein the image is sent to the processing location over the Internet.

32. A method according to claim 28, including the step of storing for comparison at least one of: (a) images that are acquired successively in times and (b) data resulting from images acquired successively in time.

33. A method of acquiring an image comprising:

providing at least one non-optical sensor, said non-optical sensor being a non-thermal sensor; and utilizing said at least one non-optical sensor to acquire an image of one of a non- dermatoglyphic zone of skin and a zone of hair;

utilizing said image to determine at least one of a parameter of said zone and a diagnosis of said zone.

34. A method of acquiring an image comprising:

providing at least one non-optical sensor, said non-optical sensor having resolution enabling relief to be detected that is smaller than or equal to 100 μm;

utilizing said at least one non-optical sensor to acquire an image of one of a non- dermatoglyphic zone of skin and a zone of hair; and utilizing said image to determine at least one of a parameter of said zone and a diagnosis of said zone.

35. A method according to claim 5, wherein the active surface includes a plurality of juxtaposed rows of individual detection cells.

36. A method according to claim 7, wherein said area is in a range of from about 0.25 cm2 to about 1 cm2.

37. A method according to claim 17, wherein the non-optical sensor has a spatial resolution in a range of from about 25 to 75 μm.

38. A method according to claim 17, wherein the non-optical sensor has a spatial resolution of approximately 50 μm.

39. A method according to claim 24, wherein the digital data is transmitted over the Internet.

40. A method as recited in claim 1, further including utilizing said image to determine at least one of a parameter of said zone and a diagnosis of said zone.

41. A method according to claim 1, wherein the step of utilizing said image includes determining a density of lines in at least one direction of the skin.

42. A method according to claim 1, wherein the image is an image of a zone of an arm, and wherein the step of utilizing said image includes determining orientations of collagen bundles relative to an axis of the arm.

43. A method as recited in claim 1, further including utilizing said image to determine information concerning aging of the skin, and wherein information concerning aging is determined by analyzing lines in the skin in at least two different directions.

44. A method as recited in claim 33, further including utilizing said image to determine at least one of a parameter of said zone and a diagnosis of said zone.

45. A method of acquiring an image comprising:

providing at least one non-optical sensor for obtaining image information concerning a zone of skin; and utilizing said at least one non-optical sensor to acquire an image of one of a non- dermatoglyphic zone of skin; and utilizing said image to determine at least one of: (a) a density of lines on the skin in at least one direction, (b) information concerning aging of the skin, and (c) orientations of collagen bundles in a region of skin on the arm relative to an axis of the arm.

46. A method according to claim 45, including utilizing said image to determine a density of lines on the skin in at least a first direction.

47. A method according to claim 45, including utilizing said image to obtain information concerning aging of the skin.

48. A method according to claim 45, wherein the image is an image of a zone of an arm, the method including utilizing the image to determine orientations of collagen bundles in the zone relative to an axis of the arm.

49. A method according to claim 45, wherein the non-optical sensor includes an active surface that is sensitive to capacitance.

50. A method according to claim 45, wherein the non-optical sensor includes a plurality of capacitive detection cells.

51. A method according to claim 45, wherein the plurality of capacitive detection cells are arranged in juxtaposed rows.

52. A method according to claim 45, including utilizing said image to determine information concerning aging of the skin, and wherein information concerning aging of the skin is determined by analyzing lines in the skin in at least two different directions.

53. A method according to claim 52, wherein the analyzing of lines includes determining a ratio of a density of lines in a first direction to a density of lines in a second direction, and wherein said first direction is substantially perpendicular to said second direction.

54. A method of acquiring an image comprising:

providing at least one non-optical sensor, said non-optical sensor having resolution enabling relief to be detected that is smaller than or equal to 100 μm;

utilizing said at least one non-optical sensor to acquire an image of a non-dermatoglyphic zone of skin; and utilizing said image to determine at least one of a parameter of said zone and a diagnosis of said zone.

* * * * *